(12) United States Patent
Johnson et al.

(10) Patent No.: US 9,310,321 B1
(45) Date of Patent: Apr. 12, 2016

(54) SYSTEM AND METHOD FOR CONDUCTING ELECTROMAGNETIC RESONANT CAVITY INSPECTION OF GUN BARRELS

(71) Applicants: Mark Johnson, West Sand Lake, NY (US); Paul J. Cote, Clifton Park, NY (US); Sara Lorene Makowiec, Troy, NY (US); Joseph Carter, Ballston Spa, NY (US)

(72) Inventors: Mark Johnson, West Sand Lake, NY (US); Paul J. Cote, Clifton Park, NY (US); Sara Lorene Makowiec, Troy, NY (US); Joseph Carter, Ballston Spa, NY (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 667 days.

(21) Appl. No.: 13/687,259

(22) Filed: Nov. 28, 2012

Related U.S. Application Data

(63) Continuation-in-part of application No. 13/071,691, filed on Mar. 25, 2011, now Pat. No. 8,818,746.

(60) Provisional application No. 61/317,774, filed on Mar. 26, 2010.

(51) Int. Cl.
*G01N 22/02* (2006.01)
*F41A 31/02* (2006.01)

(52) U.S. Cl.
CPC ............... *G01N 22/02* (2013.01); *F41A 31/02* (2013.01)

(58) Field of Classification Search
CPC ................................. F41A 31/02; G01N 22/02
See application file for complete search history.

(56) References Cited

U.S. PATENT DOCUMENTS 7,716,863 B1    5/2010  Johnson et al.

OTHER PUBLICATIONS

R. Hasenbein, "Wear and Erosion in Large Caliber Gun Barrels", 2004, Weapon and Technology Directorate RTO-MP-AVT-109, pp. 16-1 to 16-14.*
MIT Lecture course 22.09, "Resonant Cavities and Waveguides", 2004, Chapter 12—http://web.mit.edu/22.09/ClassHandouts/Charged%20Particle%20Accel/CHAP12.PDF.*
Y. Narkis, "Identification of Crack Location in Vibrating Simply Supported Beams" Journal of Sound and Vibration 172(4), 549-558 (1994).
P.F. Rizos et al., "Identification of Crack Location and Magnitude in a Cantilever Beam from the Vibration Modes", Journal of Sound and Vibration 138, 381-388, 475-488 (1990).
A.D. Dimarogons, "Vibration of Cracked Structures: A State of the Art Review", Engineering Fracture Mechanics 55(5), 831-857 (1996).
G. R. Irwin, et al., "Fundamental Aspect of Crack Growth and Fracture, Fracture, and an Advanced Treatise," vol. III. Engineering Fundamentals and Environmental Effects, edited by H. Liebowitz, Academic Press, New York, pp. 2-46 (1971).

(Continued)

*Primary Examiner* — Regis Betsch
(74) *Attorney, Agent, or Firm* — Henry S. Goldfine

(57) ABSTRACT

A system and associated method for quickly and automatically determining if the safety and performance of a gun tube have been compromised by firing damage or by an excessive number of fatigue cycles. An electromagnetic resonant cavity inspection provides a means of rapidly evaluating the health of the gun tube by monitoring the resonant frequencies that evolve from microwave signals introduced into the cavity or bore of the gun tube. This approach exploits the high sensitivity of the electromagnetic cavity resonance phenomena. Defects and degradation in the structure's cavity produce quantifiable changes in the quality factor, frequency shifts, and mode splitting.

9 Claims, 8 Drawing Sheets

(56) References Cited

OTHER PUBLICATIONS

A. Morassi, "Identification of a Crack in a Rod Based on Changes in a Pair of Natural Frequencies," Journal of Sound and Vibration, 242(4), 577-596 (2001).

A. Morassi, "A Uniqueness Result on Crack Location in Vibrating Rods," Inverse Problems in Engineering, 4, 231-254, 1997.

A. Sutin, "Application of Impulse Resonant Acoustic Spectroscopy (IRAS) for Crack Detection in Pipes," presentation at the 35th Annual Review of Progress in Quantitative Nondestructive Evaluation, Chicago, Illinois, 2008.

"http://www.amsnt.com/micro_electronics_field_inspection_vehicle.html," available at http://www.amsnt.com/micro_electronics_field_inspection_vehicle.html.

Shibata et al., "Experimental study on NDT method using electromagnetic waves," the Journal of Materials Processing Technology 161, pp. 348-352 (2005).

Abbasi et al., "Microwave Detection of Longitudinal Crack and Identification of its Location in a Straight Pipe," the Journal of Power and Energy Systems, vol. 2 No. 2 pp. 538-544 (2008).

Abbasi et al., "Detection of axial crack in the bend region of a pipe by high frequency electromagnetic waves," the International Journal of Pressure Vessels and Piping 86, pp. 764-768 (2009).

Hashizume, T., et al, Crack Detection and Method of Using Electromagnetic Waves, International Journal of Applied Electromagnetic and Mechanics 20 (2004) 171-178.

\* cited by examiner

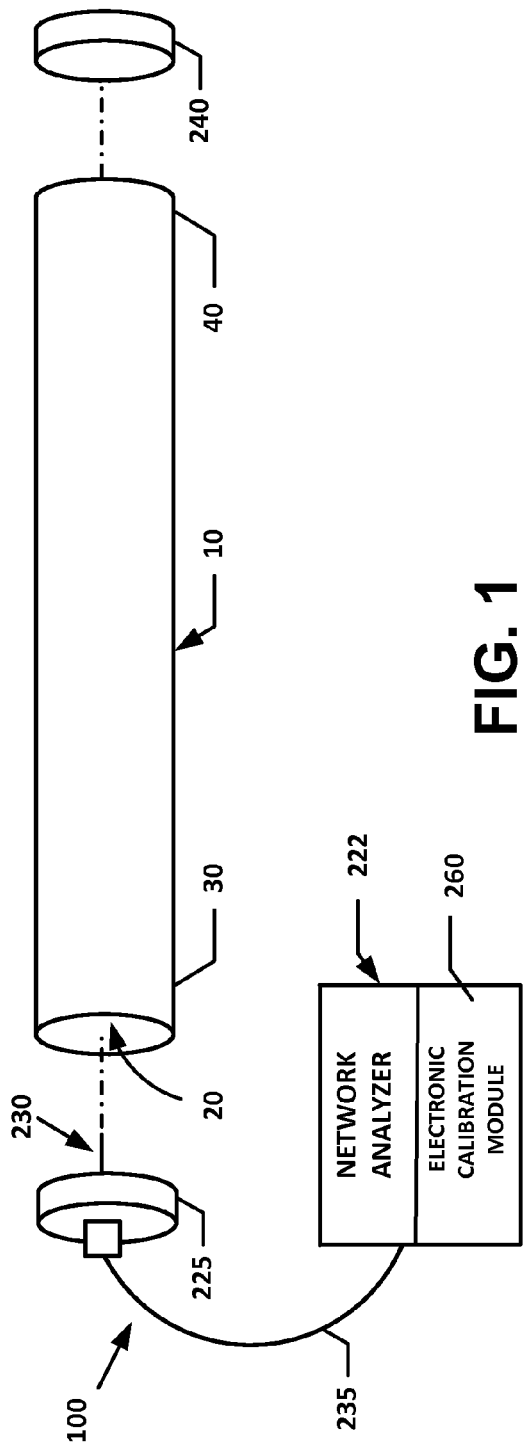
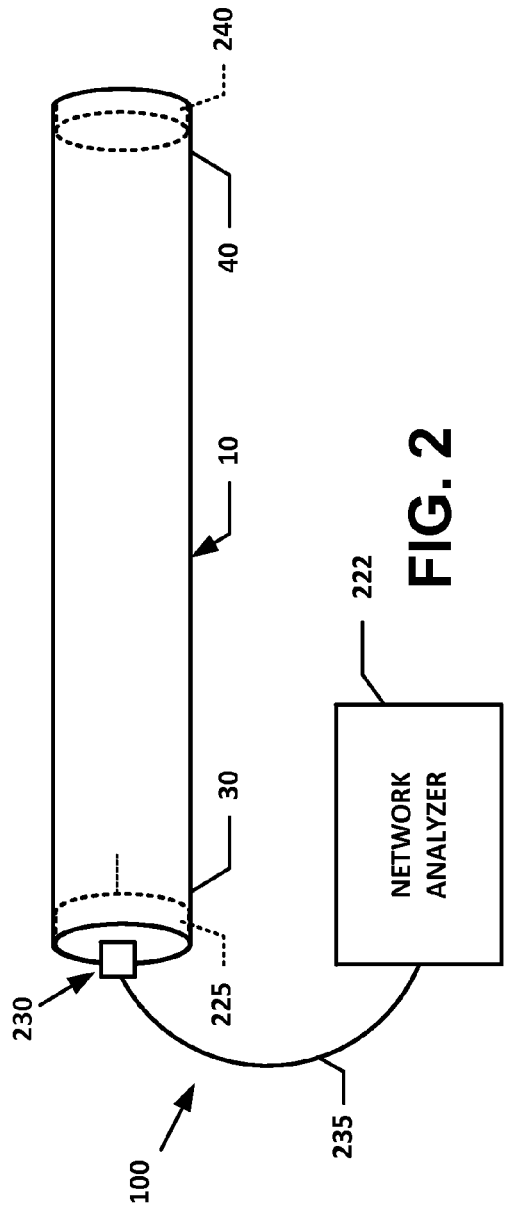

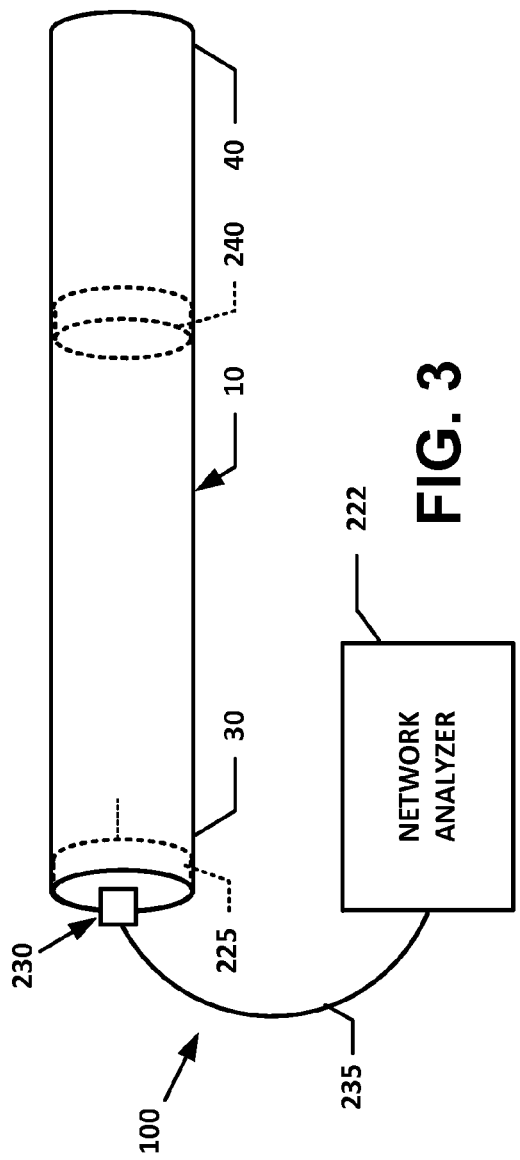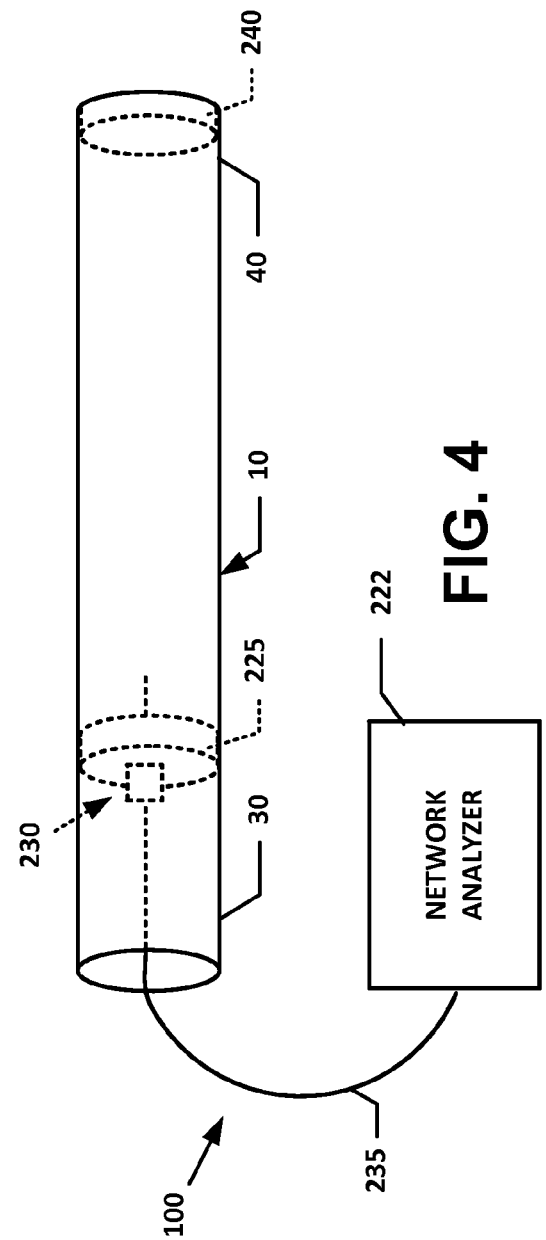

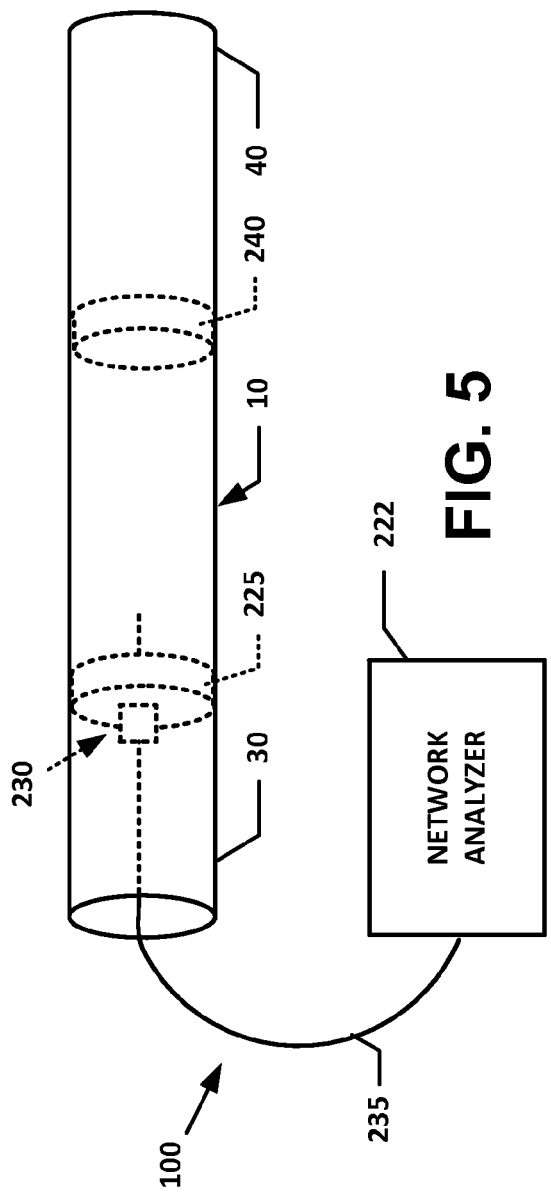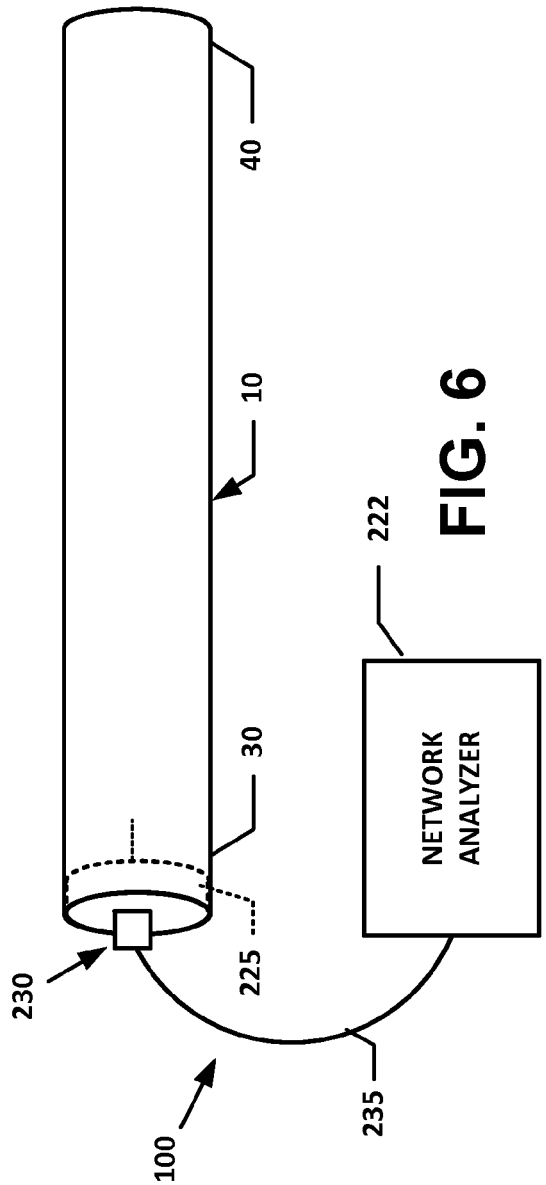

SYSTEM AND METHOD FOR CONDUCTING ELECTROMAGNETIC RESONANT CAVITY INSPECTION OF GUN BARRELS

RELATED APPLICATION

The present application is related to co-pending U.S. patent application Ser. No. 13/071,691, filed on Mar. 25, 2011, titled "Crack Detection In Thick-Walled Cylinders," which claims priority of provisional patent application, Ser. No. 61/317,774, filed on Mar. 26, 2010, and which is incorporated herein by reference in its entirety.

GOVERNMENTAL INTEREST

The invention described herein may be manufactured and used by, or for the Government of the United States for governmental purposes without the payment of any royalties thereon.

FIELD OF THE INVENTION

The present invention relates in general to the field of munitions. More specifically, this invention relates to a system and associated method for conducting an electromagnetic resonant cavity inspection of metallic cylindrically shaped tubes, such as cannon barrels, mortars, and gun barrels.

BACKGROUND OF THE INVENTION

The safety and performance of gun barrels can be compromised by use, wear, erosion, and other defects that may develop during or after manufacture, due to rough handling, under the forces related to firing, as well as under the environmental conditions and handling in the field.

Currently, the typical practice to inspect gun barrels is performed manually. However, this type of inspection is subjective and prone to operator error. Automated systems that scan the inside diameter of the gun barrels, in both manufacture and in the field, are complex, bulky, expensive, and relatively slow.

Various dynamic methods are known for identifying and quantifying structural damage as a change in fundamental resonant frequencies, which occurs as a result of such a defect in a solid structure. The change in frequencies can often be used to detect and locate the defect, even in the presence of ambient noise. A significant amount of work in the field relates to one-dimensional problems, dealing with cracked beams under axial and transverse vibration due to the ease of modeling a real beam or rod and thereby simplifying the analysis.

Particular examples of such work including a simple theory of cracked beam under axial and transverse vibrations, is described in Y. Narkis, "Identification of Crack Location in Vibrating Simply Supported Beams" Journal of Sound and Vibration 172(4), 549-558 (1994). Another work in P. F. Rizos et al., "Identification of Crack Location and Magnitude in a Cantilever Beam from the Vibration Modes", Journal of Sound and Vibration 138, 381-388, 475-488 (1990) and A. D. Dimarogonas, "Vibration of Cracked Structures: A State of the Art Review", Engineering Fracture Mechanics 55(5), 831-857 (1996), also disclose such methods and review the field of crack detection using frequency spectra.

Mathematical models are developed that simulate a crack as a linear spring for axial motion and as a torsion spring under transverse motion. The compliance of the springs is represented by the stress intensity factor based upon disclosures by G. R. Irwin, et al., "Fundamental Aspect of Crack Growth and Fracture, Fracture, and An Advanced Treatise," Vol. III. Engineering Fundamentals and Environmental Effects, edited by H. Liebowitz, Academic Press, New York, 1971, pp. 2-46. In this publication, it is shown that the natural frequencies of cracked rods and beams shift to lower values under axial or transverse loads because of the increased compliance.

A particular dynamic method was disclosed by A. Morassi, in a paper titled: "Identification of a Crack in a Rod Based On Changes in a Pair of Natural Frequencies," Journal of Sound and Vibration, 242(4), 577-596 (2001), wherein a series of calculations and experiments were presented with a hypothesis expecting more reliable results, when the damage being identified was less severe and lower order frequencies were considered. Morassi concluded that his analytical model, with these factors of less damage and lower frequencies, proved extremely accurate—the percentage discrepancy between the measured and analytical values of the involved natural frequencies being lower than 1% within the 30th vibrating mode. Morassi's method included a series of experiments using an impulse force hammer to excite a steel rod of square solid cross-section to detect notches of increasing depth (damage)—the rod suspended by two steel wire ropes to simulate free-free boundary conditions, with the axial response measured by a piezoelectric accelerometer fixed in the center of an end cross-section of the rod. The vibration signals were acquired by a dynamic analyzer and then determined in the frequency domain to measure the relevant frequency response term (inertance)—using methodology detailed in a 1997 article by A. Morassi, in Inverse Problems in Engineering, 4, 231-254, titled "A Uniqueness Result on Crack Location in Vibrating Rods".

An alternative dynamic method using impact-acoustic resonance, including Impulse Resonance Acoustic Spectroscopy (IRAS), was detailed by A. Sutin, in a presentation at the 35th Annual Review of Progress in Quantitative Nondestructive Evaluation, Chicago, Ill., 2008—the presentation titled: "Application of Impulse Resonant Acoustic Spectroscopy (IRAS) for Crack Detection in Pipes".

In IRAS, a laser vibrometer is used to detect the vibration of the specimen's surface. The spectra of the received laser signal is analyzed using FFT, to transform the signal to the frequency spectrum, such that the narrow frequency band about the specimens' resonance frequency can be filtered and isolated, and the envelope function of that filtered signal established—which will indicate a clear splitting of the resonance frequency envelope in the presence of a crack. This methodology has been demonstrated on thin-walled solid geometries, such as casing pipes, and involves significant expense.

In addition, the safety and performance of the gun systems can be compromised when the safe service life has been reached or if there is significant wear and erosion, as described earlier. The gun tube is condemned after a predetermined number of rounds have been fired or on the basis of a visual inspection.

There is currently no system that quickly and automatically determines if the wear and erosion of a fielded tube is excessive or if the gun is approaching its safe service life. The gun tubes are inspected manually (visually) at regular intervals to identify defects and changes in geometry and to determine if the wear, erosion, and defects are sufficient to warrant the removal of the tube from service. These manual visual inspection procedures using, for example borescopes, magnetic particle inspection, and pullover gages might be subjective and inefficient.

Certain military procedures, such the Weapon Record Data Cards (DA 2408-4) are used to determine if the safe service life of the tube has been reached. These cards must be accurately maintained by soldiers throughout the life of each tube and stored with the tube. If the cards are missing or incomplete, the tube must be immediately inspected or condemned, possibly prematurely. The procedures for assessing the health of a fielded gun contribute to the high operation and maintenance (O&M) costs. These O&M costs are a significant part of the military budget and are expected to increase as vehicle fleets age and as new lightweight systems are deployed.

Another conventional method for determining if the gun system is approaching the end of its safe service life, is to use an automatic round counter for some small arms. This method has also been proposed for use with other gun systems. However, the automated round counter adds additional weight, cost, size, and complexity to the gun systems. It also increases the logistic burden if it requires an external power source, such as a battery, to operate. The operational requirements of a gun system may result in an extreme thermal or shock environment that precludes the use of automated counters.

The following are exemplary round counters: The Weapon Shot Counter, available from Accu-Counter Technologies, Inc. PO Box 18038, Erlanger, Ky. 41018-0038; and the Weapon Shot Counter available from Advanced Design Consulting USA, Inc., 126 Ridge Rd, PO Box 187, Lansing N.Y. 14882. Another exemplary round counter design is described in U.S. Pat. No. 7,716,863 to Johnson et al.

Yet another conventional method to determine if the wear and erosion of a gun system is excessive or if the gun is out of tolerance is to use automated systems to detect localized defects with transducers that move across the tube surface, or that are stationary relative to a moving tube. However, these automated systems may prove to be costly, slow, and cumbersome.

An exemplary system for detecting localized defects with transducers, is the ROBINICA Robot Inspection and Calibration System that is available from Dacon A S (Postbox 133, Gamle Ringeriksvei, 1321 Stabekk, Norway). Another system is the Field Inspection Vehicle, which is generally described at: (http://www.amsnt.com/micro_electronics_field_inspection_vehicle.html), and which is developed by American Science and Technology, Benet Laboratories, and South Dakota State University. These two exemplary systems perform inspections using a tethered measurement unit inserted into the barrel. The measurement unit collects data as it traverses the bore and may also provide an output from a camera that is integral to the device, as the measurement unit performs the scanning operation.

Still another conventional method proposes the use of guided microwave signals and acoustic techniques to identify gross defects in pipes and tubes without the need for moving a transducer along the surface. However, these guided microwave signals have been shown to detect large cracks using differences in the magnitude of the reflection coefficient. This approach may lack the sensitivity to identify subtle changes in tube geometry or changes in the bore surface due to firings.

In addition, the current automated acoustic techniques that do not employ a moving transducer relative to the inside or outside of a tube surface may lack the sensitivity to detect small defects in the bore surface or changes in the bore surface properties due to firings.

In the International Journal of Applied Electromagnetics and Mechanics, Volume 20, numbers 3-4 (2004) pages 171-178, Shibata, et al. disclose a method of using electromagnetic waves for detecting cracks in pipes in a paper titled "Crack detection method using electromagnetic waves." The paper describes an approach based on the difference in the intensity microwaves for tubes with and without a crack. Tests were performed on a 34 mm diameter pipe using 2 mm thick spacers with 38 mm and 42 mm diameters to represent cracks. The crack depth was shown to correlate with the change in magnitude of the transmitted wave. A second experiment was performed showing the effect of crack position on the intensity of the reflected wave.

The Journal of Materials Processing Technology 161 (2005), pages 348-352, Shibata, et. al. discusses a similar approach in a paper titled "Experimental study on NDT method using electromagnetic waves". Abbasi, et. al disclose a microwave inspection technique in the Journal of Power and Energy Systems, vol 2 No. 2 (2008) pages 538-544 in a paper titled "Microwave Detection of Longitudinal Crack and Identification of its Location in a Straight Pipe" and in the international Journal of Pressure Vessels and Piping 86 (2009) 764-768 in a paper titled "Detection of axial crack in the bend region of a pipe by high frequency electromagnetic waves". The approach is based on the differences in the reflection coefficient (ratio of reflected to transmitted signal) between a defect-free structure and one with a crack. Crack location is determined by measuring the time-of-flight of the electromagnetic waves using the inverse fast Fourier transform of network analyzer signals.

Thus, there still remains a need for a relatively low cost and simple system and associated method for expeditiously determining if the safety and performance of a gun tube have been compromised by firing damage or by an excessive number of fatigue cycles. Prior to the advent of the present invention, the need for such a system has heretofore remained unsatisfied.

SUMMARY OF THE INVENTION

The present invention satisfies this need, and describes an electromagnetic resonant cavity system and associated method (collectively referred to herein as "the system" or "the method") for providing a means for rapidly evaluating the health of gun tubes in the field. The present method is an automated process that improves safety while reducing O&M costs. No manual visual inspection or maintenance of gun cards throughout the life of a tube is required.

The health of the gun is determined by using the tube as a cylindrical electromagnetic cavity resonator, and monitoring the resonant frequencies that evolve from microwave signals introduced into the bore of the tube (or barrel). This method exploits the high sensitivity of the electromagnetic cavity resonance phenomena. Defects and degradation in the tube produce quantifiable changes in a quality factor (Q), frequency shifts, and mode splitting (in cylindrical components). The present method uses these changes to determine the health of the gun tube.

Defects, such as pits and cracks, disrupt the symmetry of the surface, which changes the electrical properties of the tube bore (or cavity) as the field is rotated. These changes are manifested as shifts or splitting of the resonant frequencies. The degree to which the resonant frequencies shift or split directly correlates with the size of the surface defect and its location relative to a standing wave.

A fielded gun has a very tight design tolerance, and deviations can result in an unacceptable degradation in performance. The present method provides a fast, simple, and a sensitive technique for determining if the gun tube is out of tolerance. The high sensitivity is a result of the high quality factor Q associated with the efficiency of cavity resonator defined by the gun bore. Minor changes in the geometry due to wear or deformation have a predictable effect on the resonances so it is possible to determine if changes in resonance are a result of a defect or bore geometry.

Although developed to rapidly evaluate the health of a fielded gun, the present method can be also be used as an inspection tool in the manufacturing of a cylindrically shaped tube. It is a highly sensitive technique that can detect surface/rifling defects, dimensional irregularities, over-machined bore diameter, and deficiencies in coating thickness.

The material properties of the surface change each time a gun tube is fired. This may occur in tubes with or without a protective coating. In general, these changes are subtle and occur very near the bore surface. Microwave signals can be used to detect these changes because the skin depth is on the order of the depth at which these changes occur (5-10 um). This low depth of penetration ensures that only the properties of the bore surface, not those of the bulk tube, affect the cavity resonance.

One example of a change in the material properties that occur when a gun is fired is the heat checking and softening of a protective chrome coating. This changes the surface currents of the resonating cavity, which in turn, affects the energy dissipated in the bore. The quality factor Q is a measure of this effect since it is a ratio of the time averaged energy stored in the cavity to the energy loss per cycle. The change in material properties becomes more dramatic with subsequent shots so the effect on the efficiency of the cavity, reflected in the value of the quality factor Q, is greater.

BRIEF DESCRIPTION OF THE DRAWINGS

The above and other features of the present invention and the manner of attaining them, will become apparent, and the invention itself will be best understood, by reference to the following description and the accompanying drawings, wherein:

FIG. 1 is a schematic view of an electromagnetic resonant cavity system shown prior to assembly to a gun tube to be inspected, according to a first preferred embodiment of the present invention;

FIG. 2 is a schematic view of the electromagnetic resonant cavity system of FIG. 1, shown assembled to the gun tube to be inspected, according to the first preferred embodiment of the present invention;

FIG. 3 is a schematic view of the electromagnetic resonant cavity system of FIG. 1, shown assembled to the gun tube to be inspected, according to a second preferred embodiment of the present invention;

FIG. 4 is a schematic view of the electromagnetic resonant cavity system of FIG. 1, shown assembled to the gun tube to be inspected, according to a third preferred embodiment of the present invention;

FIG. 5 is a schematic view of the electromagnetic resonant cavity system of FIG. 1, shown assembled to the gun tube to be inspected, according to a fourth preferred embodiment of the present invention;

FIG. 6 is a schematic view of the electromagnetic resonant cavity system of FIG. 1, shown assembled to the gun tube to be inspected, according to a fifth preferred embodiment of the present invention;

Similar numerals refer to similar elements in the drawings. It should be understood that the sizes of the different components in the figures are not necessarily in exact proportion or to scale, and are shown for visual clarity and for the purpose of explanation.

DETAILED DESCRIPTION OF PREFERRED EMBODIMENTS

Figure 7:
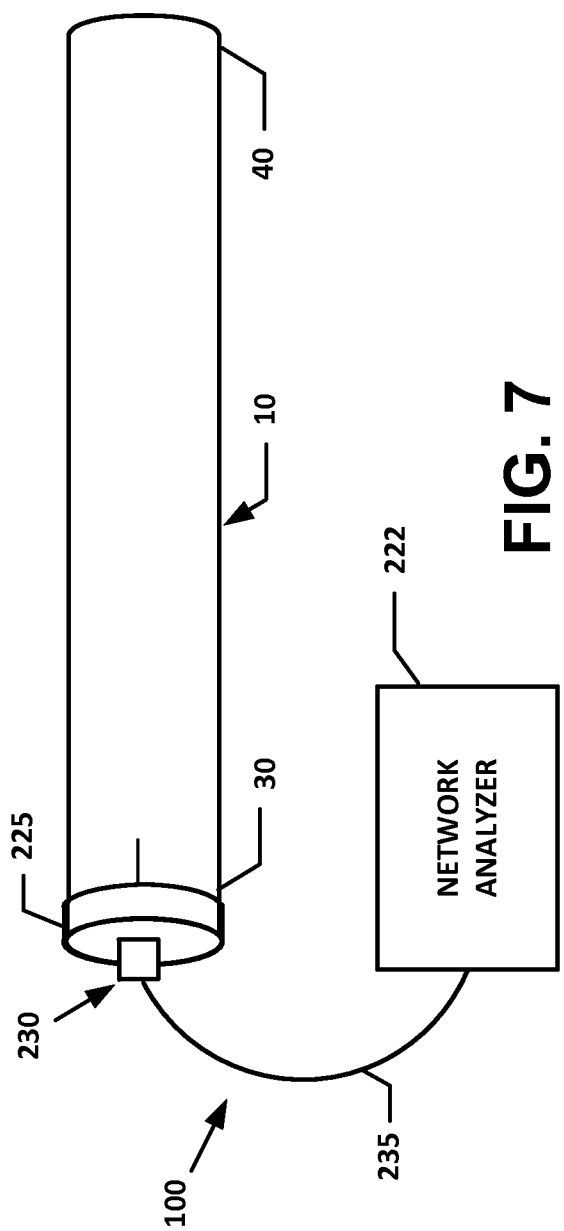
FIG. 7 is a schematic view of the electromagnetic resonant cavity system of FIG. 1, shown assembled to the gun tube to be inspected, according to a sixth preferred embodiment of the present invention.

FIG. 1 illustrates an exemplary electromagnetic resonant cavity system 100 shown prior to assembly to a gun tube 10 to be inspected, according to a first preferred embodiment of the present invention. The system 100 offers a new technique for evaluating the condition of the gun tube 10, by monitoring the resonance responses that evolve from microwave signals introduced into a bore 20 of the gun tube 10.

The system 100 presents numerous advantages, among which are the following: it is relatively simple to implement; it measures the degradation of the inner surface of the bore 20 that results from firing; it is sensitive to small surface defects; it is sensitive to small changes in the geometry of the tube; and it quickly and automatically determines if the safety and performance of the gun tube 10 have been compromised by firing damage or by an excessive number of fatigue cycles.

To this end, the system 100 generally includes a network analyzer 222 that is connected to a muzzle end cap 225. An antenna 230 is electrically connected to the network analyzer 222 by means of an electrical wiring 235. The antenna 230 is secured to the muzzle end cap 225 so that when the muzzle end cap 225 is secured to the muzzle 30 of the gun tube 10, it protrudes within the bore 20. A breech section cap 240 may optionally be included in selected embodiments, as part of the system 100, for placement either along the interior axial length of the gun tube 10, or at the breech section 40 of the gun tube 10.

FIG. 2 illustrates the electromagnetic resonant cavity system 100 of FIG. 1 assembled to the gun tube 10 to be inspected, according to a first preferred embodiment of the present invention. According to this embodiment, the muzzle end cap 225 fits inside the gun tube muzzle 30 and is located at the extremity of the muzzle 30, while the breech section cap 240 fits inside, and is placed at the breech section 40 of the gun tube 10. This embodiment enables the user to inspect defects along the entire length of the gun tube 10.

FIG. 3 illustrates the electromagnetic resonant cavity system 100 of FIG. 1 assembled to the gun tube 10 to be inspected, according to a second preferred embodiment of the present invention. According to this embodiment, the muzzle end cap 225 fits inside the gun tube muzzle 30 and is located at the extremity of the muzzle 30, while the breech section cap 240 fits inside, and is placed at distance from the breech section 40 of the gun tube 10. This embodiment enables the user to inspect defects along a section of the gun tube 10, between the muzzle end cap 225 and the breech section cap 240.

FIG. 4 illustrates the electromagnetic resonant cavity system 100 of FIG. 1 assembled to the gun tube 10 to be inspected, according to a third preferred embodiment of the present invention. According to this embodiment, the muzzle end cap 225 fits inside the gun tube muzzle 30 and is located at a distance from extremity of the muzzle 30, while the breech section cap 240 fits inside and is placed at the breech section 40 of the gun tube 10. This embodiment enables the user to inspect defects along a section of the gun tube 10, between the muzzle end cap 225 and the breech section cap 240.

FIG. 5 illustrates the electromagnetic resonant cavity system 100 of FIG. 1 assembled to the gun tube 10 to be inspected, according to a fourth preferred embodiment of the present invention. According to this embodiment, the muzzle end cap 225 fits inside the gun tube muzzle 30 and is located at a distance from the extremity of the muzzle 30, while the breech section cap 240 fits inside and is also placed at a distance from the breech section 40 of the gun tube 10. This embodiment enables the user to inspect defects along a section of the gun tube 10, between the muzzle end cap 225 and the breech section cap 240.

FIG. 6 illustrates the electromagnetic resonant cavity system 100 of FIG. 1 assembled to the gun tube 10 to be inspected, according to a fifth preferred embodiment of the present invention. According to this embodiment, the muzzle end cap 225 fits inside the gun tube muzzle 30 and is located at the extremity of the muzzle 30, while the system 100 does not include a breech section. This embodiment enables the user to inspect defects along the entire length of the gun tube 10.

FIG. 7 illustrates the electromagnetic resonant cavity system 100 of FIG. 1 assembled to the gun tube 10 to be inspected, according to a sixth preferred embodiment of the present invention. According to this embodiment, the muzzle end cap 225 fits to the outer surface the gun tube muzzle 30 and is located at the extremity of the muzzle 30, while the system 100 does not include a breech section. This embodiment enables the user to inspect defects along the entire length of the gun tube 10.

While only six exemplary embodiments have been illustrated, it should be understood that these embodiments are not exclusive and that additional embodiments may be included within the scope of the present invention.

Considering for illustration purpose only, the embodiment illustrated in FIG. 2, the network analyzer 222 determines the resonance frequency of the gun tube 10. Alternatively, this resonance frequency is pre-calculated (or pre-determined) in advance of the test, either analytically or experimentally, and then inputted to the network analyzer 222. For example purpose, the resonance frequency of the gun tube 10 is 1.915 MHz.

Similarly, the impedance of the gun tube 10 could either be determined by the network analyzer 222, or pre-determined either analytically or experimentally, and then inputted to the network analyzer 222. The impedance of the antenna 230 preferably matches that of the gun tube 10, in order to achieve maximum power at the resonance frequency. For example purpose, the impedance is approximately 50 ohms.

Next, the network analyzer 222 determines the quality factor, Q, of the gun tube 10. As it will explained later in greater detail, the resistive energy loss damps the cavity oscillations, and the quality factor, Q, is a measure of this effect.

Thereafter, the network analyzer 222 determines the radio frequency (RF) resistivity of the gun tube 10 at the resonance frequency, it be clear that the resonance frequency defines the depth, beneath the surface, that is being inspected by the system 100.

The network analyzer 222 then correlates the RF resistivity of the gun tube 10 to the number of times that the gun tube 10 has been fired, in order to determine if it should be retired from service.

Figure 9:
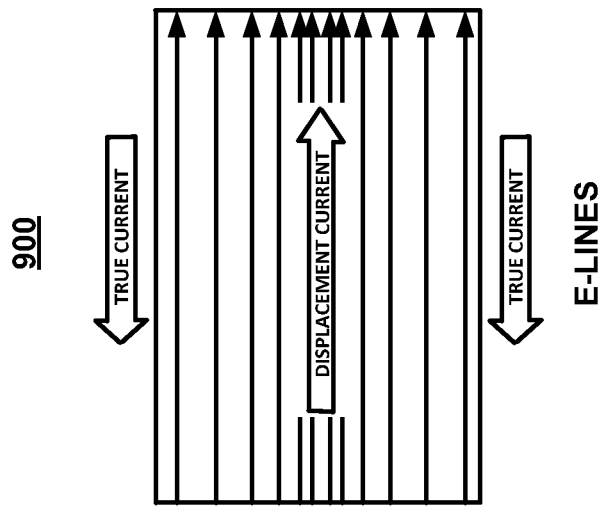
FIG. 9 is a graph of the electric field lines (E) for the TM010 mode of the cylindrical electromagnetic cavity resonator formed by the bore.
Figure 8:
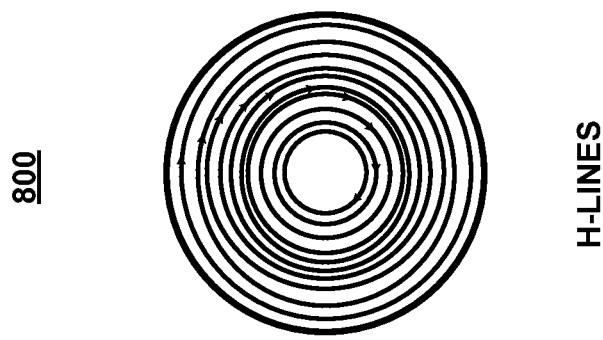
FIG. 8 is a graph of the magnetic field lines (H) for the $TM_{010}$ mode of the cylindrical electromagnetic cavity resonator formed by the bore.

The operation of the electromagnetic resonant cavity system 100 will now be described in more detail in connection with FIGS. 8, 9, 10. The cylindrical cavity defined by the gun bore 20 (FIG. 1) supports the propagation of several modes of electromagnetic (EM) waves when microwave signals are introduced into the bore 20. A technical description of the nature of these EM waves and the definition of the variables used in this description are given in Appendix A, below.

Experimental Procedure

In this exemplary experimental procedure, transverse magnetic (TM) modes (where the z component of the magnetic field is 0) are used to estimate the age of the gun tube 10 because, as is shown below, the real surface currents provide a better sampling of the properties of the bore (20) surface. The resonant TM frequencies for a gun bore 20 with a radius a and length d are given by (appendix A, equation A.26), which equation is reproduced below as equation (1):

$$f_{mnp} = \frac{1}{2\pi\sqrt{\mu_0 \epsilon_0}} \sqrt{\left(\frac{x_{mn}}{a}\right)^2 + \left(\frac{p\pi}{d}\right)^2} \quad (1)$$

In this equation, $f_{mnp}$ refers to the resonant frequencies of the cylindrical cavity resonator; $\mu_0$ refers to the permeability of free space; $\epsilon_0$ refers to the permittivity of free space; $x_{mn}$ refers to the zeros of the Bessel function (2.405 for TM010 mode); a refers to the inner radius of the bore 20; p refers to the number of complete wavelengths along the length of the bore cavity; and d refers to the length of the bore cavity. $x_{mn}$ and p are defined in more detail in Appendix A.

There is no variation in the $\rho$ or $\phi$ components (cylindrical coordinates) of the electric field E associated with the lowest frequency (m=0,n=1,p=0) TM mode, $TM_{010}$. The electric E is comprised of only an $E_z$ component with a $\rho$ dependence defined by the Bessel function $J_m(k_c\rho)$. The magnetic field lines (H) 800 and the electric field lines (E) 900 for the $TM_{010}$ mode are shown in FIGS. 8 and 9, respectively. The current associated with the $TM_{010}$ mode travels down the walls of the gun tube 10 and returns as a displacement current. This distribution of currents provides the optimal sampling of the entire bore (20) surface in the region of interest that is being inspected.

In FIG. 2, the network analyzer 222 and the stub antenna 230 were used to introduce the guided microwave signals into the gun bore 20. The antenna 230 used was stub shaped and mounted to a metal end cap 225 that is inserted into one end 30 of the gun tube 10. Another metal plug or cap 240 was inserted at the opposite end 40 to a location that defines the end of the bore surface being evaluated.

As illustrated in FIGS. 2-7, the bore (20) surface being evaluated may be the entire gun tube 10 or a particular section of interest such as a region where there is significant firing damage or particularly aggressive machining operations. Although the end cap 240 was employed in this test, open ended inspection is also possible using the system 100.

A sapphire insert can be used to enhance the resonance for localized inspection of a region of interest. Equation (1) above shows that for a given radius a, the separation between resonant peaks $f_{mnp}$ is smaller as d increases. The effect of neighboring resonances on the $TM_{010}$ resonance can reduce the accuracy of the measures used to evaluate the bore surface. Therefore, it may be desirable to evaluate smaller lengths of tube to achieve a greater separation.

In one test, the system 100 was employed to evaluate 760 mm long sections of M256 120 mm guns. The first 3 TM modes predicated by equation (1) above, for this geometry were 1.9124 GHz ($TM_{010}$), 1.9226 GHz ($TM_{011}$), and 1.9527 GHz ($TM_{012}$). FIG. 10 shows a log plot of the typical network analyzer 222 response for one of the samples. It shows $S_{11}$, which is the ratio of the reflected voltage to the transmitted voltage. Resonance is observed at 1.915 GHz, 1.936 GHz, and 1.977 GHz, which is consistent with the predicted values. FIG. 10 shows that in this test, the system 100 is more closely tuned to the cavity at the $TM_{010}$ frequency.

Figure 10:
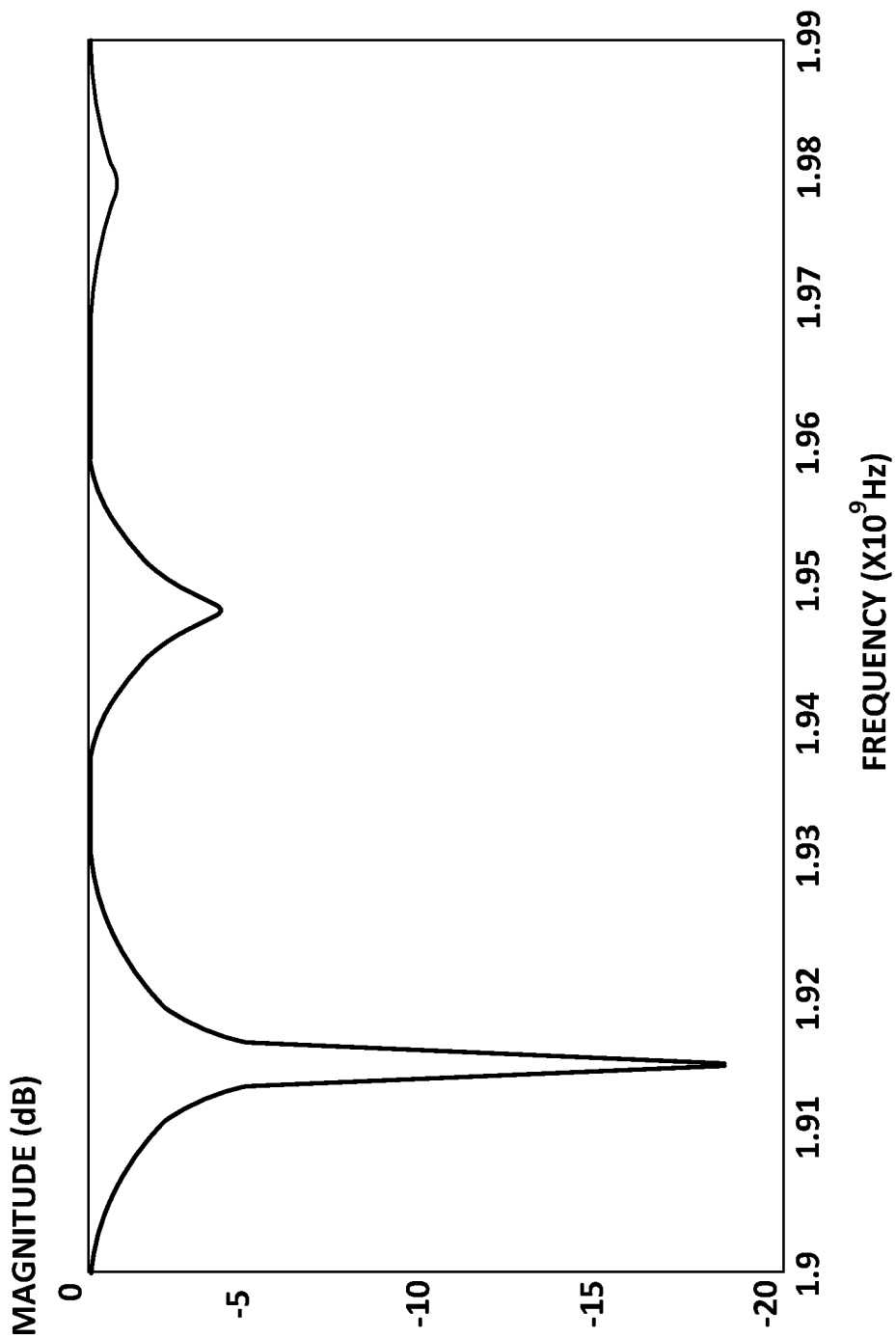
FIG. 10 is a representative log plot of the first 3 transverse magnetic modes for a sample gun tube section, as determined by the system of FIG. 2, in an experimental evaluation of the gun bore.

Since the age of a fired gun tube 10 is reflected in the degradation of the bore (20) surface, heat checking and annealing affect the propagation of the true currents along the bore surface, which in turn, alters the shape of the resonance peaks shown in FIG. 10. As these surface currents change, the energy dissipated in the bore also changes.

The resistive energy loss damps the cavity oscillations. The quality factor, Q, is a measure of this effect. Q is a measure of the loss of a resonant circuit and is defined as $2\pi$ times the ratio of the time averaged energy stored in the cavity to the energy loss per cycle, as defined in equation (2) below:

$$Q = \omega_0 \frac{\text{energy stored}}{\text{power loss}} \tag{2}$$

where $\omega_0$ is the resonance frequency.

Figure 11:
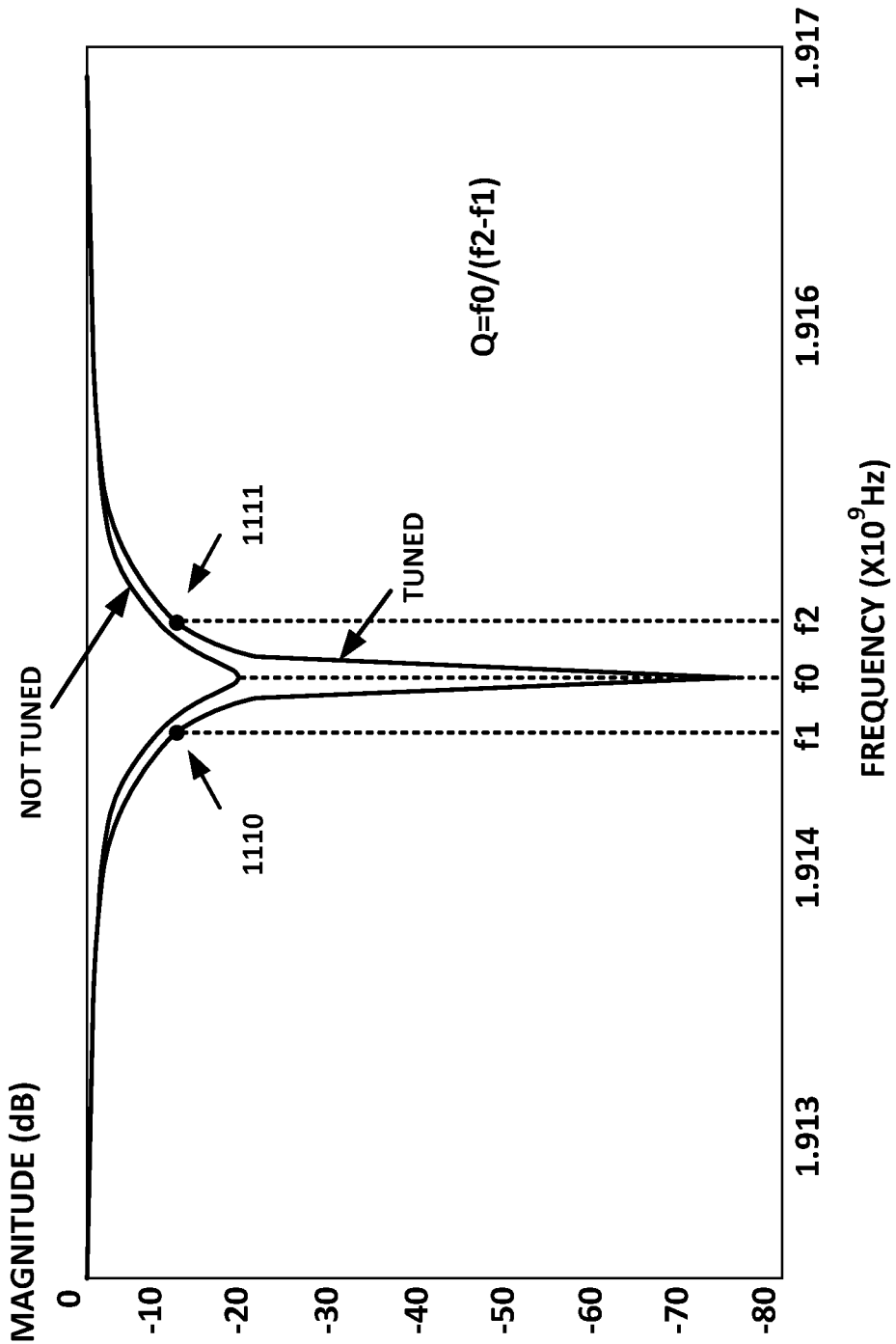
FIG. 11 is a representative plot illustrating a correction for the impedance mismatch on TM010 for a 120 mm sample.

Wither further reference to FIG. 11, since the oscillation is damped, there is no single resonance frequency, $\omega_0$, and Q is given in terms of frequencies in the neighborhood of a particular $\omega_0$. If $\Delta\omega$ is the separation between two half power points (1110, 1111), Q of the resonant cavity is defined in equation (3) below:

$$Q = \frac{\omega_0}{\Delta\omega} \tag{3}$$

Q can be estimated from signal, $S_{11}$, of the network analyzer 222, using the half power points 1110, 1111 (10.66 dB down from baseline $S_{11}$) for the bandwidth $\Delta\omega$. The analyzer signal, $S_{11}$, can be used to measure the reflection coefficient, $\Gamma$ given as shown in equation (4) below:

$$\Gamma = \frac{Z_L - Z_0}{Z_L + Z_0} \tag{4}$$

where $Z_0$ is the characteristic impedance of the ideal, infinite transmission line and $Z_L$ is the load impedance. $Z_L$ must equal $Z_0$ at resonance for critical coupling of the cavity to give reliable measures of Q. In this test, $Z_0$ is the characteristic impedance of the network analyzer 222 and cable 235 while $Z_L$ is the impedance seen at the antenna 230 that couples the signal to the bore 20. The network analyzer 222 can correct for the impedance mismatch by mathematically transforming $S_{11}$ as if the measurement was made into impedance $Z_L$ instead of the physical analyzer port impedance, $Z_0$. FIG. 11 shows the effect of this correction on $TM_{010}$ for the 120 mm samples.

The network analyzer 222 includes an electronic calibration module 260, which is used to ensure that the system 100 is calibrated from the port to the end of the cable connector. The calibration is performed across the frequency range of interest and the results stored in a calibration file that can be recalled prior to critical measurements. The algorithms for configuring the network analyzer 222, matching the impedance, and computing Q were generated as an available application running as a network analyzer macro. There is no offline analysis. Data is collected and analyzed in real-time and the results are immediately available.

In another experiment, Q was measured for sections of 38 mm diameter OFHC copper tubes, 120 mm M256 cannon sections, 60 mm mortars, and M242 Bushmaster barrels. A straight stub antenna was used to promote TM resonance and suppress the generation of other modes. The straight stub also reduced any effects due to antenna asymmetry in the estimates of Q.

In yet another experiment, the copper tubes were 237 mm long with a 37 mm diameter. Two of the copper tubes were chrome plated, one of which was annealed to 750° C. The predicted $TM_{010}$ frequency for these sections was, from equation (1), 6.20 GHz. The measured $TM_{010}$ frequency averaged 6.10 GHz. The difference can be attributed to measurement error and coating thickness. In fact, the value of the resonant frequency can be used as a tool for determining the precise geometry of the cavity. Q was determined using equation (3) with $\Delta\omega$ given by the ½ power points at 10.66 dB down, centered at 6.10 GHz. Q for the OHFC copper tube was 8494, Q for the chrome plated copper tube was 3445, and Q for the annealed chrome plated copper tube was 4859.

Equation (2) can be used to estimate the surface properties of the cavity 20 using measured values of Q. The analytic expression for ratio of the time-averaged stored energy to the energy lost per cycle in a circular cavity for TM modes is given by the following equation (5):

$$Q = \frac{2d}{\mu_r \delta \left(1 + \frac{d}{a}\right)} \tag{5}$$

where a=radius of cavity, d=length of cavity, $\mu_r$=relative permeability of the walls of the cavity, and $\delta$ is the skin depth given by equation (6):

$$\delta = \frac{1}{\sqrt{\pi \mu_0}} \sqrt{\frac{\rho}{\mu_r f}} \tag{6}$$

where $\mu_r$=relative permeability, $\rho$=RF resistivity, and f is the frequency.

Equations (5) and (6) can be used to solve for the RF resistivity, $\rho$, at the $TM_{010}$ frequency for each of the tubes. $\rho$ at 6.1 GHz for the OFHC copper tube was 393 n$\Omega$-m, $\rho$ for the chrome plated tube was 2393 n$\Omega$-m, and $\rho$ for the annealed chrome plated copper tube was 1203 n$\Omega$-m. The RF values are higher than the bulk properties of the materials because of the effect of skin depth at the higher frequency. However, the trend is similar and the results show how this approach can be used to determine surface properties of the bore 20.

Additional tests were conducted to determine the effect of annealing on ρ. A chrome plated copper tube was heated for 1 hour in 50° C. increments up to 750° C. and measured ρ at each increment. There was a nearly linear decrease in ρ at each increment. This trend was initially going to be used to correlate ρ with the number of gun firings and to provide an estimate of tube age. However, in addition to annealing of the chrome, there were a number of competing processes in 120 mm sections that occur each time the gun is fired.

The samples of 120 mm M256 tubes used for testing were chrome plated sections 0.52 m in length. Sample 1 was removed from a downbore location of a tube with relatively few fired rounds. Sample 2 was a section from a region adjacent to the chamber area of a tube with significant firing damage. The predicted and measured $TM_{010}$ frequency for each of the samples was 1.91 GHz. The measured Q for sample 1 was 6354 while Q for sample 2 was 2388. This corresponds to ρ=542 nΩ-m for sample 1 and ρ=3831 nΩ-m for sample 2. The higher resistivity associated with the fired tube (sample 2) suggests that annealing of the chrome is not the dominant mechanism that affects the surface properties when a gun is fired. The dominant mechanism is likely chromium loss from high temperature corrosion which is observed at various critical locations along a 120 mm M256 tank gun tube. This high temperature corrosion serves to undermine the chromium and facilitate chromium spallation. The exposed steel can then be rapidly consumed by the corrosion process which can produce severe pitting. These tests confirm that Q would serve as quantitative measure of an aging tube, with decreasing Q corresponding to a gradual deterioration of the coating.

In yet another test, the first 0.3 meters of rifling at the breech end of 3 chrome coated, 25 mm Bushmaster barrels were also tested. Two of the Bushmasters were proof fired (5 rounds) and one was fired 3650 times. Equation (1) was used to estimate possible resonant TM modes assuming uniform smoothbore cavities with different radii. Estimates ranged from 8.56 GHz to 9.18 GHz. Although several resonances were Observed near these frequencies, it was difficult to clearly identify the $TM_{010}$ mode. Estimates of Q were obtained at the 2 lowest resonances at which the system was most closely tuned to the cavity. The mode dependence of Q was ignored by using an average of the measured Q at these frequencies for comparison. The average Q was 2240 (4302 nΩ-m) and 2433 (3644 nΩ-m) for the unfired barrels and 912 (25954 nΩ-m) for the fired barrel. The increase in surface resistivity of the bore surface of fired barrel was consistent with the results obtained for the M256 tubes.

In still another test, five full length 60 mm mortar tubes were tested. Four of the tubes were condemned steel tubes and 1 was an unfired Inconel tube. Only 0.5 m of the bore at the breech end was evaluated to concentrate on a region where the firing damage is greatest and to provide a greater separation of the resonant peaks. The predicted $TM_{010}$ resonant frequency was 3.78 GHz which was also the measured frequency for all of the tubes. Q and (ρ) for the 4 steel tubes was 965 (52944 nΩ-m), 1032 (46293 nΩ-m), 1072 (42903 nΩ-m), and 1111 (39943 nΩ-m). Q for the Inconel tube was 3434 (4181 nΩ-m). The RF resistivity of Inconel is significantly less than steel even though the resistivity of bulk Inconel alloy 718 (1250 nΩ-m) is greater than that of 1040 steel (160 nΩ-m). This is because the relative permeability of Inconel is orders of magnitude less than that of steel. There was no firing information available on the mortars so Q could not be correlated with the number of rounds fired. However, values of Q could be used to distinguish between each of the mortars in blind tests of the technique.

The system 100 is based on resonance phenomena. Defects are identified using changes in Q and shifts or splitting of the fundamental resonant modes. The system 100 detects very small surface defects, changes in geometry, and the effects of manufacturing processes of gun tubes 10.

In these cases transverse electric (TE) resonant modes are also used to provide valuable information on the condition of the tube. The electric fields corresponding to TE modes have no component of the electric field in the z direction. Defects such as pits and cracks disrupt the symmetry of the surface which changes the electrical properties of the cavity as the field is rotated.

These changes are manifested as shifts or splitting of the resonant frequencies. The magnitude of the changes directly correlates with the size of the surface defect and its location relative to a standing wave. Large defects, or those in the proximity of a standing wave anti-node, cause greater changes than smaller defects or those near a node. Therefore, a minimum of 2 modes are preferably monitored to determine if the defect is large enough to condemn the tube 10.

According to another embodiment, the antenna 230 is an L shaped antenna that is used to promote the generation of TE modes while suppressing TM modes.

Tests were conducted on 120 mm breech sections by artificially inducing defects of various sizes. Table 1 shows shifts in $TE_{111}$ (2.08 GHz) and $TE_{112}$ (2.81 GHz) as a function of the size of the defect.

TABLE 1

Shift in frequency for different size defects

| % defect size | $\Delta TE_{111}$(kHz) | $\Delta TE_{112}$(kHz) |
|---|---|---|
| 33 | 228 | 463 |
| 67 | 322 | 825 |
| 100 | 363 | 1000 |

Figure 12:
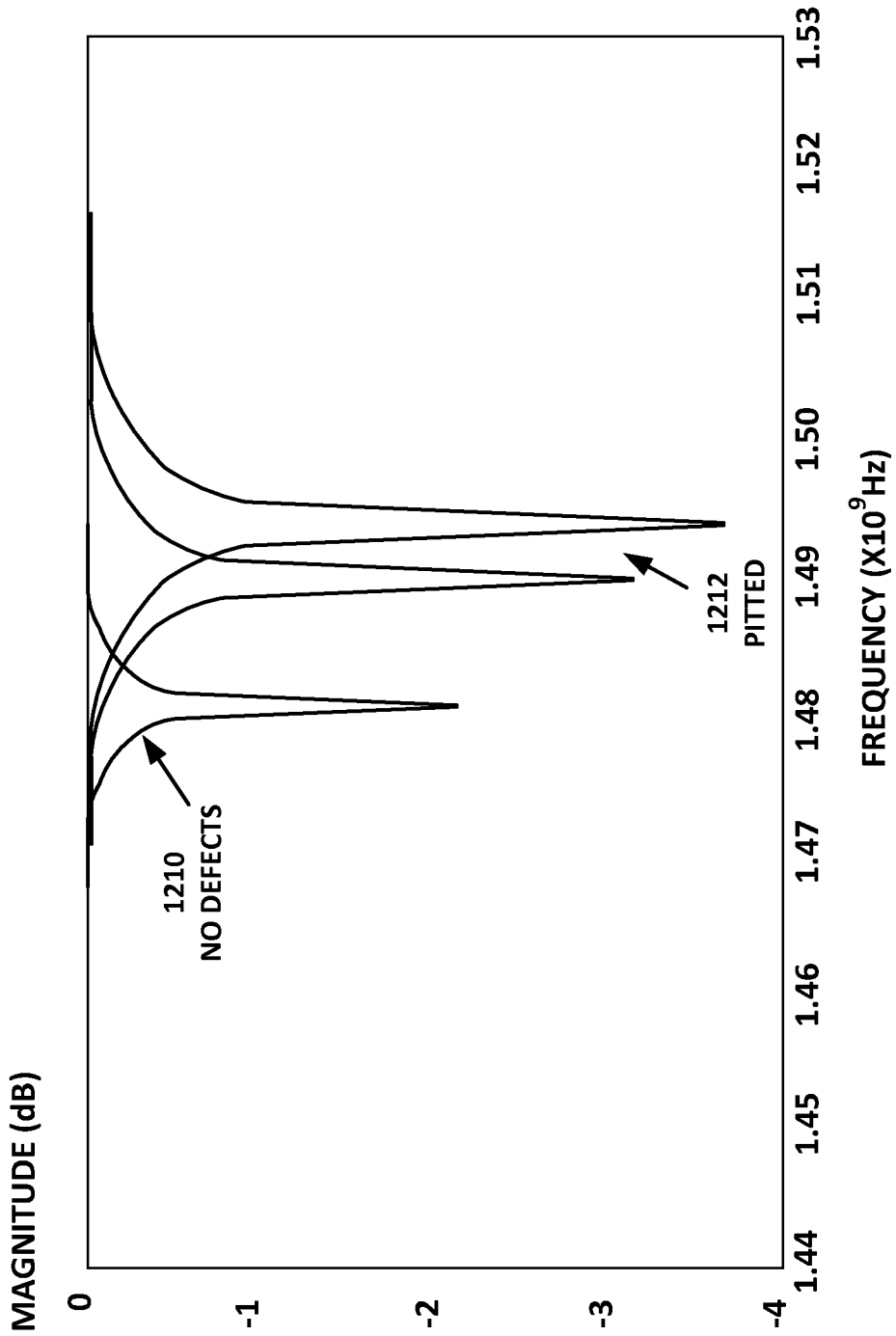
FIG. 12 is a representative plot showing a TE111 mode for undamaged and pitted 120 mm breech sections of the gun tube.

FIG. 12 is a representative plot showing S11 corresponding to the TE111 mode for a 120 mm breech section of the gun tube 10 with little (or no) firing damage (1210) and a breech section with extensive firing damage (pitting) (1212). It shows both splitting and shifting in the resonant modes for the pitted sample.

A fielded gun has a very tight design tolerance and deviations can result in an unacceptable degradation in performance. Microwave inspection provides a fast, simple, and one of the most sensitive techniques available to determine if the gun tube 10 is out of tolerance. The high sensitivity is a result of the high quality factor (Q) associated with the efficiency of cavity resonator defined by the gun bore 20. Minor changes in the geometry due to wear or deformation have a predictable effect on all of the resonances (with the possible exception of $TM_{010}$). This is unlike a surface defect that affects only a few select nodes. Therefore, it is possible to determine if changes in resonance are a result of a defect or geometry.

It should be understood that other modifications might be made to the present design without departing from the spirit and scope of the invention.

APPENDIX A

The network analyzer 222 performs the calculations based on the following analysis. The cylindrical cavity defined by a gun bore 20 supports the propagation of electromagnetic waves. Assuming a uniform bore cross-section, the spatial z dependence of these waves can be assumed to vary as $e^{-j\beta z}$, since any length l will have an identical effect on wave propagation as any other length. In this case, the phasor form of lossless transmission in the +z direction of time-harmonic electric fields given by the following equations:

$$E(\rho,\varnothing,z,t)=Re[(\hat{\rho}e_\rho e^{\Theta 1}+\hat{\varnothing}e_\varnothing e^{\Theta 2}+\hat{z}e_z e^{\Theta 3})e^{j\omega t}] \quad (A.1)$$

$$H(\rho,\varnothing,z,t)=Re[(\hat{\rho}h_\rho e^{\Theta 1}+\hat{\varnothing}h_\varnothing e^{\Theta 2}+\hat{z}h_z e^{\Theta 3})e^{j\omega t}] \quad (A.2)$$

$$E(\rho,\varnothing,z)=[e_\rho\hat{\rho}+e_\varnothing\hat{\varnothing}+e_z\hat{z}]e^{-j\beta z} \quad (A.3)$$

$$H(\rho,\varnothing,z)=[h_\rho\hat{\rho}+h_\varnothing\hat{\varnothing}+h_z\hat{z}]e^{-j\beta z} \quad (A.4)$$

Many modes of propagating electromagnetic waves are generated when microwave signals are introduced into the bore 20. Transverse magnetic (TM) modes ($H_z=0$) are employed to estimate tube age because, as is shown later, the real surface currents provide a better sampling of the properties of the bore surface. In this case, the transverse field components can be solved in terms of the longitudinal components by using the phasor form of Maxwell's equation:

$$\nabla\times E=-j\omega\mu H \quad (A.5)$$

$$\nabla\times H=j\omega\epsilon E \quad (A.6)$$

where $\mu$ is the permeability and $\epsilon$ is the permittivity of the medium. The solution for transverse field components $E_\rho=e_\rho e^{-j\beta z}$, $E_\varnothing=e_\varnothing e^{-j\beta z}$, $H_\rho=h_\rho e^{-j\beta z}$, and $H_\varnothing=h_\varnothing e^{-j\beta z}$ in terms of longitudinal field components, $E_z=e_z e^{-j\beta z}$ and $H_z=h_z e^{-j\beta z}$ is:

$$E_\rho = \frac{-j}{k_c^2}\left(\beta\frac{\partial E_z}{\partial \rho}\right) \quad (A.7)$$

$$E_\phi = \frac{-j}{k_c^2}\left(\frac{\beta}{\rho}\frac{\partial E_z}{\partial \phi}\right) \quad (A.8)$$

$$H_\rho = \frac{j}{k_c^2}\left(\frac{\omega\epsilon}{\rho}\frac{\partial E_z}{\partial \phi}\right) \quad (A.9)$$

$$H_\phi = \frac{-j}{k_c^2}\left(\omega\epsilon\frac{\partial E_z}{\partial \rho}\right) \quad (A.10)$$

where:

$$k_c^2=k^2-\beta^2 \quad (A.11)$$

and $$k=\omega\sqrt{\mu\epsilon} \quad (A.12)$$

The solution for the field components of E can be determined by taking the curl of (A.5) and solving for E from the wave equation:

$$\nabla^2 E+k^2 E=0 \quad (A.13)$$

Since each vector component of E satisfies equation (A.13), $$\nabla^2 E_z+k^2 E_z= \quad (A.14)$$

which gives:

$$\left(\frac{\partial^2}{\partial\rho^2}+\frac{1}{\rho}\frac{\partial}{\partial\rho}+\frac{1}{\rho^2}\frac{\partial^2}{\partial\phi^2}+k_c^2\right)e_z=0 \quad (A.15)$$

The general solution to (A.15) for a circular waveguide with air as a medium is:

$$e_z(\rho,\varnothing)=(A\sin(m\varnothing)+B\cos(m\varnothing))J_m(k_c\rho) \quad (A.16)$$

where $J_m(k_c\rho)$ is a Bessel function of the first kind. A and B are arbitrary constants because of azimuthal symmetry of the circular waveguide and can be 0 by proper antenna rotation at the bore. At the wall of a gun bore of radius a, $E_z(a,\varnothing)=0$, so $J_m(k_c a)=0$ and $$k_c = \frac{x_{mn}}{a}$$

where $x_{mn}$ is the $n^{th}$ root of $J_m(x_{mn})$.

From equation (A.11), the propagation constant $\beta$ is:

$$\beta = \sqrt{k^2-k_c^2} = \sqrt{k^2-\left(\frac{x_{mn}}{a}\right)^2} = \beta_n \quad (A.17)$$

wherein $\beta_{mn}$ is only real for $k>k_C$ so substituting equation (A.12) into equation (A.17) gives a cutoff frequency, $f_C$, of:

$$f_c = \frac{x_{mn}}{2\pi a\sqrt{\mu_0\epsilon_0}} \quad (A.18)$$

$E_\rho, E_\varnothing$ can be determined by substituting equation (A.16) into equations (A.7) and (A.8) to give all of the E field components:

$$E_\rho = \frac{-j\beta_{mn}}{k_c}(A\sin(m\phi)+B\cos(m\phi))J'_m(k_c\rho)e^{-j\beta_{mn}z} \quad (A.19)$$

$$E_\phi = \frac{-j\beta_{mn}n}{k_c^2\rho}(A\cos(\phi)-B\sin(m\phi))J_m(k_c\rho)e^{-j\beta_{mn}z} \quad (A.20)$$

$$E_z=(A\sin(m\varnothing)+B\cos(m\varnothing))J_m(k_c\rho)e^{-j\beta_{mn}z} \quad (A.21)$$

The direction of the travelling wave is arbitrary, so the transverse components, $E_T$, of the electric field for waves travelling in the +z direction with amplitude $A^+$, and in the −z direction with amplitude $A^-$, is given by:

$$E_T=E_\rho\hat{\rho}+E_\varnothing\hat{\varnothing}=(e_\rho\hat{\rho}+e_\varnothing\hat{\varnothing})e^{-j\beta_{mn}z}=e(\rho,\varnothing)e^{-j\beta_{mn}z} \quad (A.22)$$

$$E_T=e(\rho,\varnothing)(A^+e^{-j\beta_{mn}z}+A^-e^{j\beta_{mn}z}) \quad (A.23)$$

In the case of a resonant cavity of length d, with conducting end caps, $E_T=0$ at $z=0$ and $z=d$. Therefore, $A^+=A^-$ and $$A^+ \sin(\beta_{mn}d)=0 \tag{A.24}$$

$$\beta_{mn}d=p\pi \text{ for } p=0, 1, 2, 3, \ldots \tag{A.25}$$

Substituting equations (A.25) and (A.12) into equation (A.17) gives TM resonant frequencies:

$$f_{mnp} = \frac{1}{2\pi\sqrt{\mu_0 \epsilon_0}} \sqrt{\left(\frac{x_{mn}}{a}\right)^2 + \left(\frac{p\pi}{d}\right)^2} \tag{A.26}$$

Equation (A.26) shows that the lowest frequency TM mode is at m=0, n=1, and p=0 ($TM_{010}$). When m=0 equations (A.19-A.21) show there is no variation in any component of E with $\phi$. When p=0, then $\beta_{mn}=0$, and equations (A.19-A.20) show that $E_\rho=0$ and $E_\phi=0$. Therefore, E comprised of only an $E_z$ component with a $\rho$ dependence defined by the Bessel function $J_m(k_c\rho)$.

What is claimed is:

1. An electromagnetic resonant cavity inspection device for evaluating the health of a gun tube, comprising:
    a cap secured at a predetermined location along an inner bore of the gun tube;
    an antenna secured to the cap;
    a network analyzer that is electrically connected to the cap for introducing microwave signals into the inner bore, in order to convert the gun tube into an electromagnetic cavity resonator;
    wherein the network analyzer determines: (i) a resonance frequency, (ii) a quality factor, Q, and (iii) a radio frequency (RF) resistivity at the resonance frequency of the inner bore of the gun tube; and
    wherein the network analyzer correlates the RF resistivity to a number of fatigue cycles for the gun tube, in order to determine the health of the gun tube.

2. The electromagnetic resonant cavity inspection device of claim 1, wherein the resonance frequency defines a depth, beneath a surface of the inner bore, that is being inspected.

3. The electromagnetic resonant cavity inspection device of claim 1, wherein the quality factor Q is defined by:

$$Q = \omega_0 \frac{\text{energy stored}}{\text{power loss}}$$

where $\omega_0$ is the resonance frequency of the inner bore.

4. The electromagnetic resonant cavity inspection device of claim 1, wherein the network analyzer determines the RF resistivity by measuring an impedance of the inner bore.

5. The electromagnetic resonant cavity inspection device of claim 4, wherein the impedance of the inner bore substantially matches an impedance of the antenna, in order to achieve optimum power transfer at the resonance frequency.

6. A method for evaluating the health of a gun tube, comprising:
    securing a cap at a predetermined location along an inner bore of the gun tube;
    securing an antenna to the cap;
    electrically connecting the antenna to the cap for introducing microwave signals into the inner bore, in order to convert the gun tube into an electromagnetic cavity resonator;
    determining: (i) a resonance frequency, (ii) a quality factor, Q, and (iii) a radio frequency (RF) resistivity at the resonance frequency of the inner bore of the gun tube; and
    correlating the RF resistivity to a number of fatigue cycles for the gun tube, in order to determine the health of the gun tube.

7. The method of claim 6, wherein securing the cap at the predetermined location along the inner bore of the gun tube includes securing a first cap in proximity to one end of the inner bore.

8. The method of claim 7, wherein securing the cap at the predetermined location along the inner bore of the gun tube includes securing a second cap in proximity to another end of the inner bore.

9. The method of claim 6, wherein securing the cap at the predetermined location along the inner bore of the gun tube includes securing a first cap and a second cap within the inner bore, in order to inspect a desired section of the inner bore.

* * * * *